United States Patent
Tanzawa et al.

(10) Patent No.: US 9,494,594 B2
(45) Date of Patent: Nov. 15, 2016

(54) METHOD OF DETERMINING ADMINISTRATION EFFECT IN CANCER CHEMOTHERAPY WITH S-1

(71) Applicant: National University Corporation Chiba University, Chiba (JP)

(72) Inventors: Hideki Tanzawa, Chiba (JP); Atsushi Kasamatsu, Chiba (JP); Katsuhiro Uzawa, Chiba (JP)

(73) Assignee: National University Corporation Chiba University, Chiba (JP)

( * ) Notice: Subject to any disclaimer, the term of this patent is extended or adjusted under 35 U.S.C. 154(b) by 0 days.

(21) Appl. No.: 13/853,137

(22) Filed: Mar. 29, 2013

(65) Prior Publication Data
US 2013/0288914 A1     Oct. 31, 2013

(30) Foreign Application Priority Data
Apr. 26, 2012 (JP) ................. 2012-100681

(51) Int. Cl.
*C12Q 1/68*     (2006.01)
*G01N 33/68*     (2006.01)

(52) U.S. Cl.
CPC ....... *G01N 33/68* (2013.01); *G01N 2333/4722* (2013.01); *G01N 2800/52* (2013.01); *G01N 2800/7028* (2013.01)

(58) Field of Classification Search
CPC .................. G01N 33/68; G01N 2333/4722; G01N 2800/52; G01N 2800/7028
See application file for complete search history.

(56) References Cited

PUBLICATIONS

Yokoe et al. J Cancer Sci Ther (2010) 2: 132-135.*
Yamano et al. International Journal of Cancer 126.2 (2010): 437-449.*
Farmer et al. Nature medicine 15.1 (2009): 68-74.*
Graudens et al., Deciphering cellular states of innate tumor drug responses, Genome Biology 2006, 7:R19.*
Yamano et al., "Identification of cisplatin-resistance related genes in head and neck squamous cell carcinoma," International Journal of Cancer, vol. 126, 2010, pp. 437-449.

* cited by examiner

*Primary Examiner* — Reza Ghafoorian
(74) *Attorney, Agent, or Firm* — Kilyk & Bowersox, P.L.L.C.

(57) ABSTRACT

Provided is a method of determining a therapeutic effect of cancer chemotherapy with an anticancer drug obtained by blending three ingredients, i.e., tegafur, gimeracil, and oteracil potassium as active ingredients (hereinafter abbreviated as S-1) quickly, simply, and accurately before carrying out the cancer chemotherapy. Specifically, provided is a method of determining an administration effect in chemotherapy with S-1, the method comprising: a step (a) of measuring expression level of a decorin gene in a biological sample collected from a subject to be diagnosed; and a step (b) of determining an administration effect of S-1 based on the expression level of the gene obtained from the measurement.

7 Claims, 9 Drawing Sheets

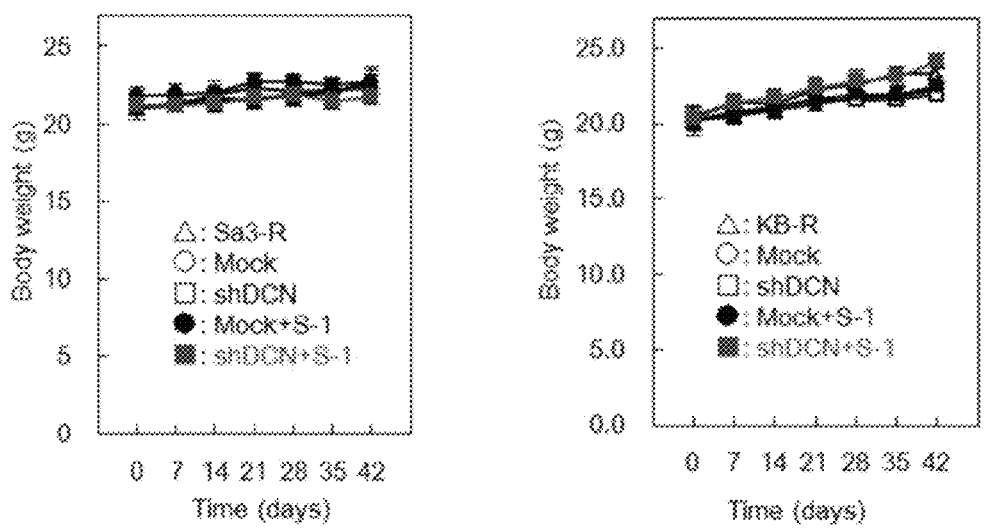

SEQUENCE LISTING

```
<160> NUMBER OF SEQ ID NOS: 2

<210> SEQ ID NO 1
<211> LENGTH: 1080
<212> TYPE: DNA
<213> ORGANISM: Homo sapiens
<220> FEATURE:
<221> NAME/KEY: misc_feature
<223> OTHER INFORMATION: human decorin gene
<220> FEATURE:
<221> NAME/KEY: CDS
<222> LOCATION: (1)..(1080)
<223> OTHER INFORMATION: human decorin gene

<400> SEQUENCE: 1 atg aag gcc act atc atc ctc ctt ctg ctt gca caa gtt tcc tgg gct      48
Met Lys Ala Thr Ile Ile Leu Leu Leu Leu Ala Gln Val Ser Trp Ala
1               5                   10                  15 gga ccg ttt caa cag aga ggc tta ttt gac ttt atg cta gaa gat gag      96
Gly Pro Phe Gln Gln Arg Gly Leu Phe Asp Phe Met Leu Glu Asp Glu
            20                  25                  30 gct tct ggg ata ggc cca gaa gtt cct gat gac cgc gac ttc gag ccc     144
Ala Ser Gly Ile Gly Pro Glu Val Pro Asp Asp Arg Asp Phe Glu Pro
        35                  40                  45 tcc cta ggc cca gtg tgc ccc ttc cgc tgt caa tgc cat ctt cga gtg     192
Ser Leu Gly Pro Val Cys Pro Phe Arg Cys Gln Cys His Leu Arg Val
    50                  55                  60 gtc cag tgt tct gat ttg ggt ctg gac aaa gtg cca aag gat ctt ccc     240
Val Gln Cys Ser Asp Leu Gly Leu Asp Lys Val Pro Lys Asp Leu Pro
65                  70                  75                  80 cct gac aca act ctg cta gac ctg caa aac aac aaa ata acc gaa atc     288
Pro Asp Thr Thr Leu Leu Asp Leu Gln Asn Asn Lys Ile Thr Glu Ile
                85                  90                  95 aaa gat gga gac ttt aag aac ctg aag aac ctt cac gca ttg att ctt     336
Lys Asp Gly Asp Phe Lys Asn Leu Lys Asn Leu His Ala Leu Ile Leu
            100                 105                 110 gtc aac aat aaa att agc aaa gtt agt cct gga gca ttt aca cct ttg     384
Val Asn Asn Lys Ile Ser Lys Val Ser Pro Gly Ala Phe Thr Pro Leu
        115                 120                 125
```

```
gtg aag ttg gaa cga ctt tat ctg tcc aag aat cag ctg aag gaa ttg      432
Val Lys Leu Glu Arg Leu Tyr Leu Ser Lys Asn Gln Leu Lys Glu Leu
    130                 135                 140 cca gaa aaa atg ccc aaa act ctt cag gag ctg cgt gcc cat gag aat      480
Pro Glu Lys Met Pro Lys Thr Leu Gln Glu Leu Arg Ala His Glu Asn
145                 150                 155                 160 gag atc acc aaa gtg cga aaa gtt act ttc aat gga ctg aac cag atg      528
Glu Ile Thr Lys Val Arg Lys Val Thr Phe Asn Gly Leu Asn Gln Met
                165                 170                 175 att gtc ata gaa ctg ggc acc aat ccg ctg aag agc tca gga att gaa      576
Ile Val Ile Glu Leu Gly Thr Asn Pro Leu Lys Ser Ser Gly Ile Glu
            180                 185                 190 aat ggg gct ttc cag gga atg aag aag ctc tcc tac atc cgc att gct      624
Asn Gly Ala Phe Gln Gly Met Lys Lys Leu Ser Tyr Ile Arg Ile Ala
        195                 200                 205 gat acc aat atc acc agc att cct caa ggt ctt cct cct tcc ctt acg      672
Asp Thr Asn Ile Thr Ser Ile Pro Gln Gly Leu Pro Pro Ser Leu Thr
210                 215                 220 gaa tta cat ctt gat ggc aac aaa atc agc aga gtt gat gca gct agc      720
Glu Leu His Leu Asp Gly Asn Lys Ile Ser Arg Val Asp Ala Ala Ser
225                 230                 235                 240 ctg aaa gga ctg aat aat ttg gct aag ttg gga ttg agt ttc aac agc      768
Leu Lys Gly Leu Asn Asn Leu Ala Lys Leu Gly Leu Ser Phe Asn Ser
                245                 250                 255 atc tct gct gtt gac aat ggc tct ctg gcc aac acg cct cat ctg agg      816
Ile Ser Ala Val Asp Asn Gly Ser Leu Ala Asn Thr Pro His Leu Arg
            260                 265                 270 gag ctt cac ttg gac aac aac aag ctt acc aga gta cct ggt ggg ctg      864
Glu Leu His Leu Asp Asn Asn Lys Leu Thr Arg Val Pro Gly Gly Leu
        275                 280                 285 gca gag cat aag tac atc cag gtt gtc tac ctt cat aac aac aat atc      912
Ala Glu His Lys Tyr Ile Gln Val Val Tyr Leu His Asn Asn Asn Ile
290                 295                 300 tct gta gtt gga tca agt gac ttc tgc cca cct gga cac aac acc aaa      960
Ser Val Val Gly Ser Ser Asp Phe Cys Pro Pro Gly His Asn Thr Lys
305                 310                 315                 320 aag gct tct tat tcg ggt gtg agt ctt ttc agc aac ccg gtc cag tac     1008
Lys Ala Ser Tyr Ser Gly Val Ser Leu Phe Ser Asn Pro Val Gln Tyr
                325                 330                 335 tgg gag ata cag cca tcc acc ttc aga tgt gtc tac gtg cgc tct gcc     1056
Trp Glu Ile Gln Pro Ser Thr Phe Arg Cys Val Tyr Val Arg Ser Ala
            340                 345                 350 att caa ctc gga aac tat aag taa                                      1080
Ile Gln Leu Gly Asn Tyr Lys
        355

<210> SEQ ID NO 2
<211> LENGTH: 359
<212> TYPE: PRT
<213> ORGANISM: Homo sapiens

<400> SEQUENCE: 2

Met Lys Ala Thr Ile Ile Leu Leu Leu Leu Ala Gln Val Ser Trp Ala
1               5                   10                  15

Gly Pro Phe Gln Gln Arg Gly Leu Phe Asp Phe Met Leu Glu Asp Glu
            20                  25                  30

Ala Ser Gly Ile Gly Pro Glu Val Pro Asp Asp Arg Asp Phe Glu Pro
        35                  40                  45

Ser Leu Gly Pro Val Cys Pro Phe Arg Cys Gln Cys His Leu Arg Val
    50                  55                  60
```

```
Val Gln Cys Ser Asp Leu Gly Leu Asp Lys Val Pro Lys Asp Leu Pro
65                  70                  75                  80

Pro Asp Thr Thr Leu Leu Asp Leu Gln Asn Asn Lys Ile Thr Glu Ile
                85                  90                  95

Lys Asp Gly Asp Phe Lys Asn Leu Lys Asn Leu His Ala Leu Ile Leu
                100                 105                 110

Val Asn Asn Lys Ile Ser Lys Val Ser Pro Gly Ala Phe Thr Pro Leu
            115                 120                 125

Val Lys Leu Glu Arg Leu Tyr Leu Ser Lys Asn Gln Leu Lys Glu Leu
            130                 135                 140

Pro Glu Lys Met Pro Lys Thr Leu Gln Glu Leu Arg Ala His Glu Asn
145                 150                 155                 160

Glu Ile Thr Lys Val Arg Lys Val Thr Phe Asn Gly Leu Asn Gln Met
                165                 170                 175

Ile Val Ile Glu Leu Gly Thr Asn Pro Leu Lys Ser Ser Gly Ile Glu
                180                 185                 190

Asn Gly Ala Phe Gln Gly Met Lys Lys Leu Ser Tyr Ile Arg Ile Ala
            195                 200                 205

Asp Thr Asn Ile Thr Ser Ile Pro Gln Gly Leu Pro Pro Ser Leu Thr
            210                 215                 220

Glu Leu His Leu Asp Gly Asn Lys Ile Ser Arg Val Asp Ala Ala Ser
225                 230                 235                 240

Leu Lys Gly Leu Asn Asn Leu Ala Lys Leu Gly Leu Ser Phe Asn Ser
                245                 250                 255

Ile Ser Ala Val Asp Asn Gly Ser Leu Ala Asn Thr Pro His Leu Arg
                260                 265                 270

Glu Leu His Leu Asp Asn Asn Lys Leu Thr Arg Val Pro Gly Gly Leu
            275                 280                 285

Ala Glu His Lys Tyr Ile Gln Val Val Tyr Leu His Asn Asn Asn Ile
        290                 295                 300

Ser Val Val Gly Ser Ser Asp Phe Cys Pro Pro Gly His Asn Thr Lys
305                 310                 315                 320

Lys Ala Ser Tyr Ser Gly Val Ser Leu Phe Ser Asn Pro Val Gln Tyr
                325                 330                 335

Trp Glu Ile Gln Pro Ser Thr Phe Arg Cys Val Tyr Val Arg Ser Ala
            340                 345                 350

Ile Gln Leu Gly Asn Tyr Lys
        355
```

METHOD OF DETERMINING ADMINISTRATION EFFECT IN CANCER CHEMOTHERAPY WITH S-1

This application claims the benefit of earlier filed Japanese Patent Application No. 2012-100681, filed Apr. 26, 2012, incorporated in its entirety by reference herein.

TECHNICAL FIELD

The present invention relates to a method of determining an administration effect in cancer chemotherapy with an anticancer drug obtained by blending three ingredients, i.e., tegafur, gimeracil, and oteracil potassium as active ingredients (hereinafter abbreviated as S-1). More specifically, the present invention relates to a method of determining an administration effect of S-1 prior to carrying out cancer chemotherapy with S-1. Still more specifically, the present invention relates to a method comprising: measuring expression level of a decorin gene in a biological sample derived from a cancer patient; and determining an administration effect in cancer chemotherapy with S-1 based on the expression level of the gene.

BACKGROUND ART

S-1 is an oral chemotherapeutic drug obtained by blending three ingredients, i.e., tegafur, gimeracil, and oteracil potassium, which is generally and widely used as neoadjuvant chemotherapy in head and neck squamous cell carcinoma, gastrointestinal cancer, and other types of cancers. Among the ingredients, tegafur is a prodrug of 5-fluorouracil (hereinafter abbreviated as 5-FU), and inhibits DNA biosynthesis, thereby exhibiting an anticancer action. Gimeracil selectively inhibits a metabolizing enzyme of 5-FU to increase a 5-FU concentration, thereby augmenting an antitumor effect. Further, oteracil potassium is distributed mainly in a gastrointestinal tissue and shows an action of alleviating gastrointestinal tissue impairment.

The present inventors reported that a tumor reduction effect was found in 61.2% of patients who received neoadjuvant chemotherapy with S-1 monochemotherapy ("Journal of Cancer Science and Therapy," 2010, 2(5), p. 132-135). However, administration effects of S-1 vary depending on patients. Therefore, in some cases, patients with no clinical effect suffer from side effects and have poor prognosis.

In cancer chemotherapy, it is known in general that incidence of side effects due to a chemotherapeutic drug is observed in many patients, and that some patients do not show any response to the chemotherapeutic drug. Therefore, there often occurs such a situation that even though many patients suffer from serious side effects, no therapeutic effect can be obtained, resulting in cancer progression and poor prognosis. Presence of resistance to the cancer chemotherapy is well known at the present time. For the purpose of reversing chemotherapeutic drug resistance, various researches have been made on a mechanism thereof and a drug for augmenting an effect of chemotherapy (e.g., "Cancer Research," 2004, 64 (22), p. 8167-8176, "Experimental Cell Research," 2003, 288 (2), p. 403-414, "International Journal of Oncology," 2003, 22(5), p. 945-953, "Biochimica et Biophysica Acta," 2002, 1587(2-3), p. 194-205, and "Anticancer Research," 2008, 28, p. 9-14 and Japanese Patent Application Laid-open No. 2009-242378 and Japanese Patent Application Laid-open No. 2011-102255).

For the purpose of selecting a chemotherapeutic drug suitable for a patient to be subjected to chemotherapy, a method of determining a therapeutic effect of a chemotherapeutic drug is carried out in some cases prior to its administration. For example, in advanced medical therapy, a method comprising using a cell culture technology has been carried out as means for collecting a cancer tissue from a cancer patient and assessing whether cancer cells contained in the cancer tissue are resistant or sensitive to a chemotherapeutic drug. Specifically, there has been carried out a method comprising: collecting a cancer tissue from a cancer patient; separating cancer cells from the cancer tissue; culturing the cancer cells using a cell culture technology; adding a chemotherapeutic drug, i.e., an anticancer drug prepared at each concentration to a culture solution of the cancer cells at the stage in which the cancer cells grow to some extent; and measuring whether the cancer cells are sensitive or resistant to the anticancer drug based on growth of the cancer cells. However, a diagnosis method comprising such a technique for culturing cancer cells as described above is rarely utilized as a diagnosis method in a clinical field because it takes 3 to 4 days to obtain diagnosis results and the technique for cell culture is complicated.

In view of the foregoing, an attempt has been made to develop a method of determining quickly a therapeutic effect of a chemotherapeutic drug prior to its administration. The inventors of the present application also disclosed methods of determining a therapeutic effect of cisplatin based on gene expression (International Patent WO2008/047947A and Japanese Patent Application Laid-open No. 2009-247309). Specifically, the inventors disclosed, as the methods of determining a therapeutic effect of cisplatin, a method comprising: measuring expression level of at least one gene selected from a phosphodiesterase 3B gene, a platelet derived growth factor C gene, a polycystic kidney disease-2 gene, a neuregulin 1 gene, and a lumican gene; and carrying out determination based on the expression level; and a method comprising: measuring expression level of at least one gene among 195 kinds of genes such as a decorin gene in addition to the above-mentioned genes; and carrying out determination based on the expression level.

Decorin (hereinafter sometimes abbreviated as DCN) is a small proteoglycan that is produced by fibroblasts. A proteoglycan is a protein having one or more glycosaminoglycan chains. A core protein of decorin has a molecular weight of about 40,000 Da, and its sequence has already been determined.

DCN is known to be an extracellular matrix protein and regulate cell-cell adhesion and cell movement through collagen fibril formation and stabilization, thereby participating in wound healing and inflammatory responses. Further, it has been reported that DCN binds to an epidermal growth factor receptor (hereinafter abbreviated as EGFR) on a cell membrane, thereby participating in various functions such as cell growth and apoptosis via a mitogen-activated protein kinase (hereinafter abbreviated as MAPK) pathway and a phosphatidylinositol 3-kinase/AKT (hereinafter abbreviated as PI3K/AKT) pathway (see FIG. 1 and "The Journal of Biological Chemistry," 2011, 286, p. 34712-34721, "NEOPLASIA," 2009, 11(10), p. 1042-1053, and "The International Journal of Biochemistry and Cell Biology," 2008, 40, p. 2120-2128).

Hitherto, in order to determine a therapeutic effect of chemotherapy with S-1 prior to its administration, there has been used a method comprising: culturing cancer cells collected from a cancer tissue of a cancer patient in the presence of S-1; and determining responsiveness of the cancer cells to S-1 based on growth of the cancer cells. However, such determination method requires much time and involves a complicated cell culture technique, resulting in a low utility value for many patients as a diagnosis method in a clinical field. Hence, the method is rarely utilized in a clinical field and has not yet been put into practical use.

SUMMARY OF INVENTION

An object of the present invention is to provide a method of determining quickly, simply, and accurately a therapeutic effect of cancer chemotherapy with S-1 prior to carrying out the chemotherapy.

The present inventors has made intensive studies in order to achieve the object. It has been found that cancer cells exhibiting resistance to a chemotherapeutic drug expresses a resistance-related gene. Accordingly, the inventors tried to provide a method comprising: identifying an S-1 resistance-related gene; and detecting the gene or a protein encoded by the gene, thereby determining a therapeutic effect of S-1 quickly, simply, and accurately.

Then, the inventors found that the expression of a DCN gene was related with S-1 resistance. Specifically, analysis of the DCN gene was performed for its expression in an anticancer drug-resistant cell line having a function of resistance to 5-FU or cisplatin. As a result, the expression of the DCN gene was found to be remarkably enhanced in the anticancer drug-resistant cell line. Meanwhile, it was observed that suppression of the expression of the DCN gene in the resistant cell line by transfecting the resistant cell line with short hairpin RNA (hereinafter abbreviated as shRNA) specific for the gene resulted in an increase in sensitivity to 5-FU. Further, as a result of verification of an administration effect of S-1 using nude mice implanted with the resistant cell line and the resistant cell line with suppressed expression of DCN (hereinafter abbreviated as shDCN cell line), a significant decrease in tumor volume was found in the shDCN cell line-implanted mice as compared to the resistant cell line-implanted mice. In the shDCN cell line, a significant decrease was found in the amount of phosphorylated AKT by the administration of S-1, which revealed that the suppressed expression of DCN and the administration of S-1 inhibited the phosphorylation of AKT involved in the induction of apoptosis, leading to the promotion of apoptosis. As described above, the inventors clarified in in vitro and in vivo experimental systems that the suppressed expression of DCN was related with a reduction in anticancer drug resistance.

The inventors also found that the expression of DCN in a clinical analyte had a correlation with a rate of response for S-1.

The inventors identified the DCN gene as the S-1 resistance-related gene based on the above-mentioned research results, and thus accomplished the present invention.

That is, the present invention relates to a method of determining an administration effect in chemotherapy with S-1, the method comprising:

a step (a) of measuring expression level of a DCN gene in a biological sample collected from a subject to be diagnosed; and a step (b) of determining an administration effect of S-1 based on the expression level of the gene obtained from the measurement.

In addition, the present invention relates to the above-identified method of determining an administration effect in chemotherapy with S-1, in which the step (a) comprises measuring a protein that is a product of the gene.

Further, the present invention relates to the above-identified method of determining an administration effect in chemotherapy with S-1, in which the step (a) comprises measuring an amount of mRNA of the gene.

Further, the present invention also relates to the above-identified method of determining an administration effect in chemotherapy with S-1, in which the biological sample is a biological sample collected before carrying out the chemotherapy with S-1.

In addition, the present relates to the above-identified method of determining an administration effect in chemotherapy with S-1, in which the biological sample is a biological sample collected from a cancer patient.

Further, the present invention relates to the above-identified method of determining an administration effect in chemotherapy with S-1, in which the biological sample is a biological sample collected from a head and neck squamous cell carcinoma patient, an esophageal squamous cell carcinoma patient, or a lung squamous cell carcinoma patient.

Further, the present invention also relates to a method of determining an administration effect in chemotherapy with S-1, the method comprising:

a step (a) of measuring an expression amount of a DCN protein in a biological sample collected from a head and neck cancer patient before carrying out chemotherapy with S-1; and a step (b) of determining an administration effect of S-1 based on the expression amount of the DCN protein obtained from the measurement.

In addition, the present invention relates to a method of determining an administration effect in chemotherapy with S-1, the method comprising:

a step (a) of measuring an expression amount of a decorin protein in a biological sample collected from a head and neck cancer patient before carrying out chemotherapy with S-1 by immunohistological staining using an anti-decorin protein antibody; and a step (b) of determining an administration effect of S-1 using a cutoff value for an immunohistochemical staining (IHC) score obtained from the measurement, wherein the cutoff value is 119.

Further, the present invention relates to a method of determining an administration effect in chemotherapy with an anticancer drug, the method comprising:

measuring expression level of a decorin gene in a biological sample collected from a subject to be diagnosed; and determining an administration effect of an anticancer drug based on the expression level of the gene obtained from the measurement, wherein the anticancer drug is obtained by blending 5-FU as an active ingredient.

Advantages of the Invention

According to the present invention, the method of determining an administration effect in chemotherapy with S-1 can be provided, wherein the method comprising: a step (a) of measuring expression level of a DCN gene in a biological sample collected from a subject to be diagnosed; and a step (b) of determining an administration effect of S-1 based on the expression level of the gene obtained from the measurement.

The method of determining an administration effect in chemotherapy with S-1 according to the present invention enables the determination of resistance or sensitivity to S-1, and allows the determination of presence or absence of a response to the administration of S-1 in simple, quick, and objective manner with high accuracy. Thus, by carrying out the method of determining an administration effect in chemotherapy with S-1 according to the present invention, it can be determined whether or not treatment comprising administering S-1 is applied to a patient of interest.

As described above, the present invention enables a determination of therapeutic effect of chemotherapy with S-1 prior to its administration. Hence, the present invention can provide an improvement in quality of life (hereinafter abbreviated as QOL) important for a patient and a contribution to a reduction in medical cost.

BRIEF DESCRIPTION OF THE DRAWINGS

FIG. 7 shows the results of measurement of a change in body weight in order to evaluate toxicity of the administration of S-1 and the suppressed expression of DCN on the mice in the in vivo experiment in which the S-1 sensitivity of the shDCN cell line-derived tumor was verified; there was no significant change in body weights of the mice by the administration of S-1 and the suppressed expression of DCN.

FIG. 8 shows the results of staining of the tumor tissues implanted into the mice by a TUNEL method in the in vivo experiment in which the S-1 sensitivity of the shDCN cell line-derived tumor was verified; a clear increase in apoptosis was found in a group which was implanted with the shDCN cell line and orally administered with S-1 as compared to other groups.

DETAILED DESCRIPTION OF THE INVENTION

Figure 1:
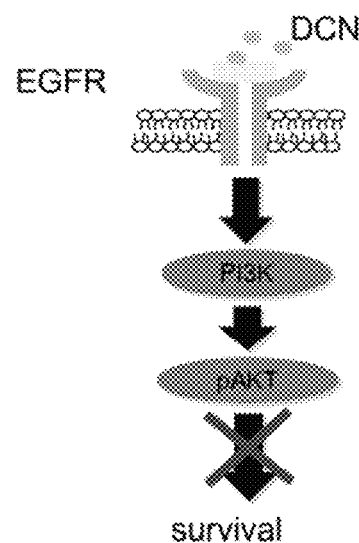
FIG. 1 is a characteristic diagram of a pathway illustrating that DCN is involved in cell growth and apoptosis; DCN binds to an EGFR on a cell membrane, thereby participating in cell survival through a PI3K/AKT pathway that is one of the pathways responsible for cell apoptosis.

An embodiment of the present invention is described in detail below. It should be noted that the present invention is by no means limited thereto.

A method of determining an administration effect in chemotherapy with S-1 according to the present invention comprises: a step (a) of measuring expression level of a DCN gene in a biological sample collected from a subject to be diagnosed; and a step (b) of determining an administration effect of S-1 based on the expression level of the gene obtained from the measurement.

S-1 is an anticancer drug obtained by blending tegafur, gimeracil, and oteracil at a molar ratio of 1:0.4:1. Specific examples of such anticancer drug may include TS-1™, a product of TAIHO PHARMACEUTICAL CO., LTD. A chemotherapeutic drug which is applied to the method of determining an administration effect in chemotherapy with S-1 according to the present invention is not particularly limited as long as the chemotherapeutic drug is an anticancer drug obtained by blending the three ingredients, i.e., tegafur, gimeracil, and oteracil potassium as active ingredients, but is preferably an anticancer drug obtained by blending tegafur, gimeracil, and oteracil at a molar ratio of 1:0.4:1.

A nucleotide sequence of the DCN gene and an amino acid sequence of a protein encoded by the gene have already been reported. A nucleotide sequence of a human DCN gene and an amino acid sequence of a protein encoded by the gene are set forth in SEQ ID NOS: 1 and 2 of the sequence listing, respectively, which are registered at GenBank under Accession No. AF138300 (VERSION: AF138300.1 GI: 5532410).

The subject to be diagnosed is not particularly limited and may be any of patients suffering from various types of cancers, persons suspected to have malignant cancer, and healthy persons. Further, the method of determining an administration effect in chemotherapy with S-1 according to the present invention is carried out by using a biological sample collected from the subject to be diagnosed, not by subjecting the subject to be diagnosed directly to any treatment.

The biological sample is not particularly limited as long as it can be used for analysis of gene expression in the subject to be diagnosed, and examples thereof may include a tissue, cell, body fluid, and urine isolated from the subject to be diagnosed, and a mixture thereof. The term "body fluid" as used herein is meant to encompass blood, a lymph fluid, tissue fluids (an interstitial fluid, an intercellular fluid, and an interstitial fluid), a coelomic fluid, a chorionic cavity fluid, a pleural fluid, an ascitic fluid, a pericardial effusion fluid, a cerebrospinal fluid (spinal fluid), a joint fluid (synovial fluid), humor aqueous (aqueous humour), a digestive fluid, a pancreatic fluid, an intestinal fluid, a seminal fluid, and a amniotic fluid. In addition, the biological sample to be used may be any one kind or more selected from a tissue, a cell, a body fluid, urine, and other biological protein extracts.

The biological sample is preferably a sample containing cancer cells or a sample suspected of containing cancer cells, and may be preferably exemplified by part of a tissue obtained upon surgery performed for the purpose of treating a cancer patient, and part of a tissue collected by biopsy or the like from a subject to be diagnosed as being suspected to have cancer.

The biological sample is preferably a biological sample collected before carrying out chemotherapy with S-1. The use of such biological sample enables the prediction of resistance or sensitivity to S-1 before carrying out chemotherapy with S-1. As a result, it can be carried out to determine whether or not treatment including administration of S-1 is applied to a subject to be diagnosed, that is, to screen a subject to whom treatment including administering S-1 is applied.

The biological sample may be a protein extract or nucleic acid extract prepared from, for example, a tissue, cell, body fluid, or urine isolated from a subject to be diagnosed and a mixture thereof. The preparation of the protein extract or the nucleic acid extract may be carried out by utilizing a protein preparation method or nucleic acid preparation method known per se.

The measurement of the expression of the DCN gene in the biological sample collected from the subject to be diagnosed is specifically carried out, for example, by measuring the amount of mRNA for a gene to be measured or by measuring the amount of a protein that is a gene product to be measured.

A known protein detection method may be used as a method of measuring the amount of the protein that is the gene product to be measured. Specifically, various methods using an antibody against the protein to be measured are applicable.

It should be noted that a human-type antibody, a mouse antibody, a rat antibody, a rabbit antibody, a sheep antibody, or the like may be appropriately used as the antibody as long as the protein to be measured serves as an antigen and the antibody binds to the antigen. The antibody may be a polyclonal antibody or a monoclonal antibody, and is preferably a monoclonal antibody from the viewpoint of stably producing a homogeneous antibody. The polyclonal antibody and the monoclonal antibody may each be produced by a method well known to a person skilled in the art. Further, a desired antibody selected from commercially available antibodies may also be utilized.

A hybridoma that produces the monoclonal antibody may be basically produced by using a known technology as described below. That is, the hybridoma may be produced by: using an antigen of interest or a cell expressing the antigen of interest as a sensitizing antigen; immunizing a desired animal with the sensitizing antigen to obtain an immunocyte by using a general immunization method; subjecting the immunocyte to fusion to a known parental cell by a general cell fusion method; and then screening a desired monoclonal antibody-producing cell (hybridoma cell) by a general screening method. The production of the hybridoma may be carried out, for example, by referring to the method of Milstein et al. ("Methods of Enzymology," 1981, 73, p. 3-46).

In this connection, in the production of the monoclonal antibody, the above-mentioned gene product may be used as the antigen. Further, a cell expressing a fragment of the above-mentioned gene product may be used as the antigen. It should be noted that any such protein or fragment of the protein can be easily acquired by a person skilled in the art by referring to a method described in a literature such as Sambrook et al. Ed., "Molecular Cloning: A Laboratory Manual," 2nd Edition, Vol. 1 to 3, Cold Spring Harbor Laboratory Press, New York, 1989. Further, the cell expressing any such protein or fragment of the protein can also be easily acquired by a person skilled in the art by referring to the above-mentioned method.

The resultant monoclonal antibody may be used as a test drug for quantifying a protein to be measured in an enzyme-linked immunosorbent assay (ELISA), an enzyme immunodot assay, a radioimmunoassay, an aggregation-based assay, or any other known immunoassay method. Further, the monoclonal antibody is desirably labeled. Upon the labeling, a labeling compound to be used is exemplified by an enzyme, a fluorescent substance, a chemiluminescent substance, a radioactive substance, a staining substance, or the like known in the art.

The protein or the antibody may also be immobilized on a support before use for quantifying the protein. The support has only to be, for example, one on which a protein can be immobilized. In general, examples thereof may include an inorganic material such as a glass sheet, a silicon wafer, and a resin, or a natural polymer material such as nitrocellulose, or a synthetic polymer material such as nylon or polystyrene.

A known method of detecting gene expression may be used as a method of measuring the amount of mRNA for a gene to be measured. For example, the measurement of the amount of mRNA may be carried out by using any of a northern blotting method, a polymerase chain reaction (PCR), real-time-PCR (RT-PCR), a hybridization method, a DNA array method, and the like. Further, the measurement of the amount of mRNA may be carried out by a known method comprising using, as a probe, a polynucleotide having a DNA sequence that hybridizes with a gene to be measured under a stringent condition. For example, in the production of the probe, the probe is appropriately labeled with a fluorescent label or the like in advance, and the labeled probe is made to hybridize with mRNA isolated and purified from a biological sample collected from a subject to be diagnosed, or cDNA synthesized from the mRNA. After that, the intensity of fluorescence derived from the hybridized probe is measured to allow detection of the amount of mRNA in the gene to be measured. It should be noted that the probe may also be used by being immobilized on a support such as glass beads or a glass substrate. That is, the probe may be used in the form of a DNA chip or microarray in which the probe produced for the gene to be measured is immobilized on the support. The support is not particularly limited and may be of any shape or material as long as a polynucleotide can be immobilized thereon. In general, examples of the support may include an inorganic material such as a glass sheet, a silicon wafer, and a resin, or a natural polymer material such as nitrocellulose, or a synthetic polymer material such as nylon.

The polynucleotide to be immobilized on the support may also be a synthetic oligonucleotide. Further, a nucleic acid derivative which may be subjected to fluorescent labeling may be introduced into a sequence of the synthetic oligonucleotide. Further, a so-called Affymetrix type DNA chip technology capable of synthesizing an oligonucleotide of interest on a support may also be used. In addition, a desired polynucleotide may be spotted and immobilized on a columnar surface of a so-called type of 3D-Gene, a product of Toray Industries, Inc. including a support having a three-dimensional structure.

It should be noted that the phrase "hybridizes under a stringent condition" means that hybridization is maintained, for example, even when washing treatment at 42° C. with a buffer containing 1×SSC (0.15 M NaCl and 0.015 M sodium citrate) and 0.1% sodium dodecyl sulfate (SDS) at 42° C. is performed. It should be noted that various elements except the above-mentioned temperature condition are known as elements that affect the stringency of the hybridization, and a person skilled in the art can combine the various elements to realize stringency equivalent to the stringency of the hybridization exemplified above.

A probe and a primer set for quantitatively detecting mRNA or cDNA derived from the DCN gene are not particularly limited as long as the mRNA or cDNA can be specifically detected. The probe and the primer set may be appropriately designed based on nucleotide sequence information on the DCN gene, and may be acquired by synthesis in accordance with a conventional method. Further, a desired prove and primer may be selected and utilized from commercially available primers and probes for detecting the DCN gene.

In the method of determining an administration effect of S-1 according to the present invention, after measuring the expression level of the DCN gene in the biological sample collected from the subject to be diagnosed as described above, the presence or absence of an effect of the administration of S-1 or the degree of the effect is determined based on the expression level.

Specifically, after measuring the expression level of the DCN gene by any one of the above-mentioned methods, the expression level of the gene is evaluated. The evaluation of the expression level may be performed by setting a reference value and carrying out comparison with the reference value. An amount of constitutive expression of a gene can be set as the reference value, and the evaluation of the expression level can be performed by a relative value to the reference value. When the expression level of the DCN gene in the biological sample collected from the subject to be diagnosed is high as compared to the reference value, the subject to be diagnosed can be assessed to have resistance to S-1. In contrast, when the expression level of the DCN gene in the biological sample collected from the subject to be diagnosed is low as compared to the reference value, the subject to be diagnosed can be assessed to have sensitivity to S-1.

The measurement of the expression level of the DCN gene may also be performed by immunohistochemical staining (hereinafter sometimes abbreviated as IHC) or immunocytochemical staining (sometimes abbreviated as ICC) as shown in Examples described later. The resultant score may be used to perform evaluation, and a score which enables to determine false positive and false negative cases may be used as the reference value. The IHC and the ICC are each a method comprising allowing an antibody that specifically binds to a substance having antigenicity, mainly a protein, to act on the substance to cause an antigen-antibody reaction, thereby detecting the substance in a tissue or in a cell. The method comprising using a tissue as a sample to be tested is called IHC, and the method involving using a cell as a sample to be tested is called ICC. As the antibody for detection, there is used one labeled in advance with, for example, an enzyme that produces a substance which can be visualized such as a fluorescent dye or an insoluble pigment. That enables the detection of the substance to be easily carried out.

An IHC score is a total sum of numbers obtained by multiplying the percentage of positive cells in all cells in one field of view in observation with an objective lens having a magnification of 40 by the intensity of staining property. The intensity of staining property is evaluated, for example, on a three-point scale, i.e., "weak," "medium," and "strong," and the respective evaluations are assigned with integers of 1 to 3 to be converted to numerical values. This procedure is performed for 10 visual fields sampled at random, and an average value thereof is calculated as the IHC score. The IHC score is generally used in a method of determining staining degree at present as an excellent score showing a staining intensity and a staining range.

When measuring the expression level of the DCN gene by IHC to evaluate the expression level, a cutoff value for the IHC score may be used as a reference value. Specifically, the cutoff value may be exemplified by 100 to 120, preferably 105 to 120, more preferably 110 to 120, still more preferably 115 to 120, yet still more preferably 119. That is, when the IHC score of DCN is equal to or less than the cutoff value, it is determined that a biological sample showing such an IHC score has high sensitivity to the administration of S-1, and thus an effect of the administration of S-1 can be expected.

According to the method of determining an administration effect in chemotherapy with S-1 according to the present invention, the presence or absence of an effect of the administration of S-1 on a subject to be diagnosed or the degree of the effect can be assessed with very excellent sensitivity and excellent specificity. Herein, the sensitivity means a positive rate in a group of patients showing a response to the administration of S-1. Further, the specificity means a negative rate in a group of patients not showing any response to the administration of S-1.

According to the method of determining an administration effect in chemotherapy with S-1 according to the present invention, an effect of the administration of S-1 can be determined in a more objective and specific manner by gene expression analysis, e.g., expression analysis at an mRNA level or a protein level using a biological sample collected from a cancer patient before the start of anticancer drug administration or chemotherapy. Thus, such administration of S-1 as to impose an excessive burden on a patient on whom an administration effect cannot be expected can be prevented, and information of a therapeutic strategy useful for the patient can be provided.

An object which is applied to the method of determining an administration effect in chemotherapy with S-1 according to the present invention is not particularly limited as long as the object is cancer envisaged to be treated by the administration of S-1 as an option of treatment, and may be exemplified by head and neck cancer, esophagus cancer, lung cancer, stomach cancer, biliary tract cancer, bile duct cancer, liver cancer, pancreas cancer, large bowel cancer, preferably head and neck squamous cell carcinoma, esophageal squamous cell carcinoma, and lung squamous cell carcinoma.

The method of determining an administration effect in chemotherapy with S-1 according to the present invention also allows to carry out the determination of an administration effect of an anticancer drug obtained by blending 5-FU as an active ingredient similarly to the determination of the administration effect of S-1.

Hereinafter, the present invention is described in detail by way of examples. However, the technical scope of the present invention is by no means limited to the following examples.

Example 1

Expression Analysis of DCN in Anticancer Drug-Resistant Cell Lines

Cancer cell lines exhibiting function of drug resistance to 5-FU and cisplatin ("International Journal of Cancer," 2010, 126(2), p. 437-449) were used as anticancer drug-resistant cell lines. Specifically, anticancer drug-resistant cell lines Sa-3R, H-1R, and KB-R respectively established from oral squamous cell carcinoma-derived cell lines Sa-3 and H-1 and a head and neck squamous cell carcinoma-derived cell line KB were used.

Figure 2:
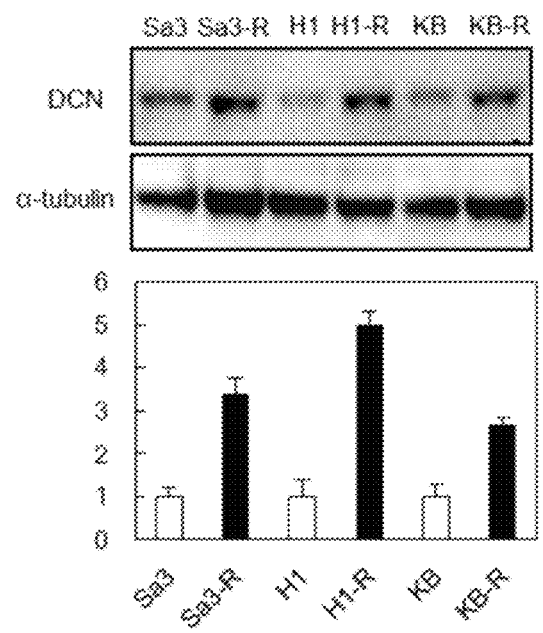
FIG. 2 shows the results of detection of the expression of DCN in anticancer drug-resistant cell lines and their parental lines by Western blotting; the expression of DCN was found to be enhanced in the anticancer drug-resistant cell lines Sa-3R, H-1R, and KB-R as compared to the parental lines.

First, the expression analysis of DCN in the anticancer drug-resistant cell lines and their parental lines was performed by protein detection using Western blotting. Specifically, a protein separated by sodium dodecyl sulfate-polyacrylamide gel electrophoresis (SDS-PAGE) was transferred to a nitrocellulose membrane, followed by blocking with skim milk. After that, the resultant was subjected to a reaction with an anti-human DCN rabbit polyclonal antibody (product of Santa Cruz Biotechnology, Inc.) at a dilute concentration of 1:1,000 at room temperature for 2 hours, sufficiently washed, and subjected to a reaction with a horseradish peroxidase (HRP)-labeled anti-rabbit secondary antibody at a dilute concentration 1:2,500 at room temperature for 1 hour. Then, a light-emitting band was confirmed. Further, the expression analysis of α-tubulin as an endogenous loading control was similarly performed. As a result, as shown in FIG. 2, the enhanced expression of DCN was found in the anticancer drug-resistant cell lines. There was no difference in the expression of α-tubulin.

Example 2

Suppressed Expression of DCN and Reduction in Degree of Anticancer Drug Resistance (In Vitro Experiment)

A relation between the expression level of DCN and the degree of anticancer drug resistance was investigated using an in vitro experimental system. The anticancer drug-resistant cell lines Sa-3R and KB-R were used as cancer cells, in which the enhanced expression of DCN was found at high level. Further, cells with suppressed expression of DCN in the above-mentioned anticancer drug-resistant cell lines were produced. Those cells were cultured in the presence of an anticancer drug and compared for their degrees of resistance to the anticancer drug.

Specifically, the anticancer drug-resistant cell lines Sa-3R and KB-R were transfected with DCN shRNA to suppress the expression of DCN in the cell lines. Decorin shRNA Plasmid (h) (catalog No. SC-40993-SY), a product of Santa Cruz Biotechnology, Inc., was used as DCN shRNA. Control shRNA Plasmid-A (catalog No. SC-108060), a product of Santa Cruz Biotechnology, Inc., was used as control shRNA. Lipofectamine (product of Life Technologies Corporation) was used as a transfection reagent.

The Sa-3R line and the KB-R line were transfected with DCN shRNA (product of Santa Cruz Biotechnology, Inc.). The lines were subjected to selection in a selective medium containing neomycin at 1.0 µg/ml to 1.5 µg/ml to select a cell colony in which the expression of DCN was stably suppressed. Then, the expression of mRNA and a protein was analyzed by RT-PCR and Western blotting. Further, in the analysis of mRNA, the expression analysis of α-tubulin as an endogenous loading control was similarly performed. In the Western blotting, the analysis of glyceraldehyde-3-phosphate dehydrogenase (GAPDH) as an endogenous control was similarly performed, and DCN protein in each cell line was evaluated by a value for relative expression to GAPDH protein.

Figure 3:
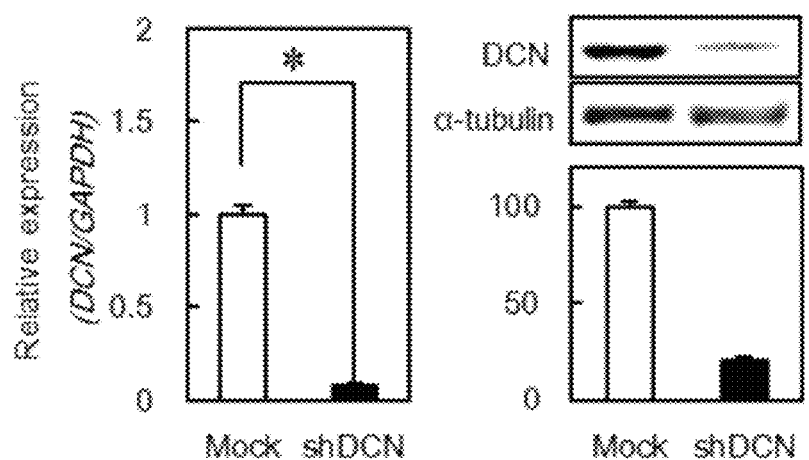
FIG. 3 shows the results of measurement of the expression of DCN in an anticancer drug-resistant cell line which was transfected with short hairpin RNA specific for DCN (hereinafter abbreviated as DCN shRNA) and thereby suppressed in expression of DCN (hereinafter referred to as shDCN cell line); the right figures show the results of detection of DCN mRNA by RT-PCR; the left figure shows the results of measurement of the amount of a DCN protein by Western blotting; the anticancer drug-resistant cell line transfected with DCN shRNA showed significant reduction in the amount of the mRNA and the amount of the protein as compared to an anticancer drug-resistant cell line transfected with a vector alone (hereinafter referred to as Mock cell line).

As shown in FIG. 3, significant reductions in the mRNA amount and protein amount of DCN were observed in the shDCN cell line as compared to the Mock cell line. Experiments to be described later were performed using a stable cell line in which the expression of DCN was certainly suppressed.

First, the presence or absence of a change in cell growth ability by the transfection with DCN shRNA was studied. The shDCN cell line was seeded at $1\times10^5$ cells/1 ml of medium/3 cm of dish, and cultured in the presence or absence of 5-FU for 24 hours to 120 hours. After that, trypsinization was performed, and the number of cells was counted. The Mock cell line was used as a control.

Figure 4:
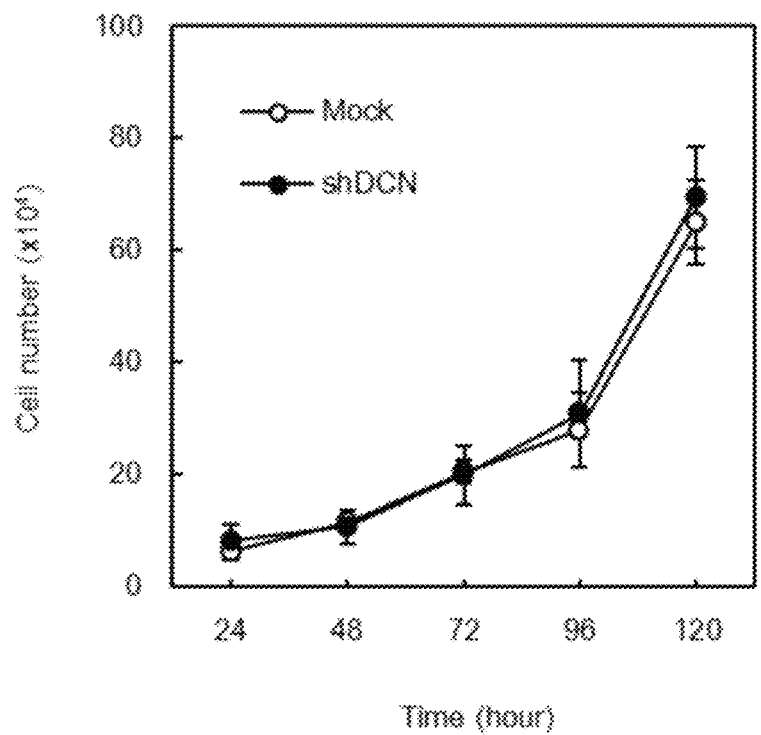
FIG. 4 shows the results of verification of the presence or absence of changes in cell growth ability by the transfection of the anticancer drug-resistant cell lines with DCN shRNA; there was no significant difference in cell growth ability between the Mock cell line and the shDCN cell line throughout the entire period for which counting was performed.

As shown in FIG. 4, there was no significant difference in cell growth ability by the transfection with shDCN throughout the entire period for which the counting was performed.

Next, the shDCN cell line and the Mock cell line were cultured in the presence of an anticancer drug, and a change in the degree of resistance to the anticancer drug by the suppressed expression of DCN was verified by measuring a change in cell growth ability. 5-FU was used as the anticancer drug.

The shDCN cell line and the Mock cell line were each seeded to a 96-well plate at a density of $2\times10^3$ cells/100 µl of medium/well, and simultaneously mixed with 10 µl of a medium supplemented with 5-FU. The concentration of 5-FU was adjusted so that the final concentration was 1 µM to $1\times10^4$ µM. After that, the cells were incubated for 72 hours, and a cell survival rate was evaluated by an MTS assay. An MTS solution (product of Promega Corporation) was added at a volume of 10 µl/well, and the cells were incubated for 4 hours. After that, counting was performed with a plate reader at a wavelength of 490 nm. A 50% survival concentration (IC50) was determined based on the results of, the MTS assay.

Figure 5:
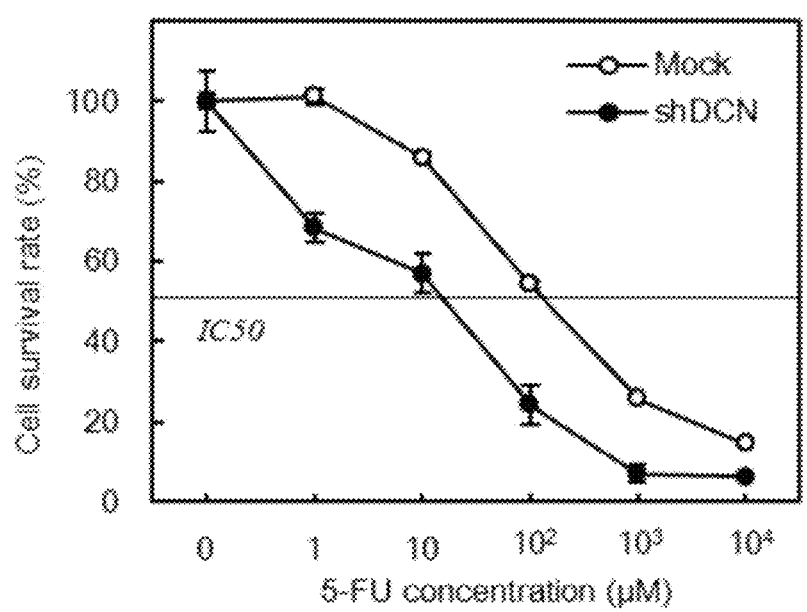
FIG. 5 shows the results of 5-FU sensitivity tests on the shDCN cell line and the Mock cell line; the shDCN cell line showed an IC50 value about 10 times lower than that of the Mock cell line; in other words, the shDCN cell line showed about 10 times increased sensitivity to 5-FU.

As shown in FIG. 5, the shDCN cell line showed an IC50 value about 10 times lower than that of the Mock cell line. The fact revealed that the shDCN cell line had increased sensitivity to 5-FU by about 10 times. That is, it can be considered that the suppressed expression of DCN reduced the resistance of the anticancer drug-resistant cell line to 5-FU.

Example 3

Suppressed Expression of DCN and Reduction in Degree of Anticancer Drug Resistance (In Vivo Experiment)

A relation between the expression level of DCN and the degree of anticancer drug resistance was investigated using an in vivo experimental system using nude mice (inbred BALB/c nude mice: product of Charles River Laboratories International, Inc.) which were implanted with a tumor derived from cells with suppressed expression of DCN. An animal experiment was performed in conformity with the guidelines of the Canadian Council on Animal Care (CCAC). All the mice were female, purchased at 4 weeks of age, and used for the experiment at 6 weeks of age.

Inoculated cell lines were anticancer drug-resistant cell lines Sa-3R and KB-R, and shDCN cell lines and Mock cell lines thereof. A cell suspension obtained by diluting each of the cell lines to $1\times10^7$ cells/200 µl with phosphate buffered saline (PBS) was subcutaneously injected to the back of the mice using a 29G needle (Myjector: product of TERUMO CORPORATION). The tumor-inoculated mice were observed every 3 days, and the mice having a tumor volume of 100 to 300 mm³ were assigned to an experimental group. The evaluation of the tumor volume was performed by measuring the length and width of a tumor and calculating the tumor volume from the measured length and width with the following expression: (length×width²)/2.

S-1 was used as the anticancer drug. The oral administration of S-1 was performed for 14 consecutive days at a concentration of 2 mg/kg/day for the mice inoculated with the Sa-3R line and the KB-R line, and the Mock cell lines and shDCN cell lines thereof. During the experimental period, feed and water were provided ad libitum. As the evaluation of the toxicity of the administration of S-1 and the suppressed expression of DCN on the mice, an increase or decrease in body weight was observed. The measurement of the body weights of the mice was performed at the time of the measurement of the tumor sizes thereof.

Figure 6:
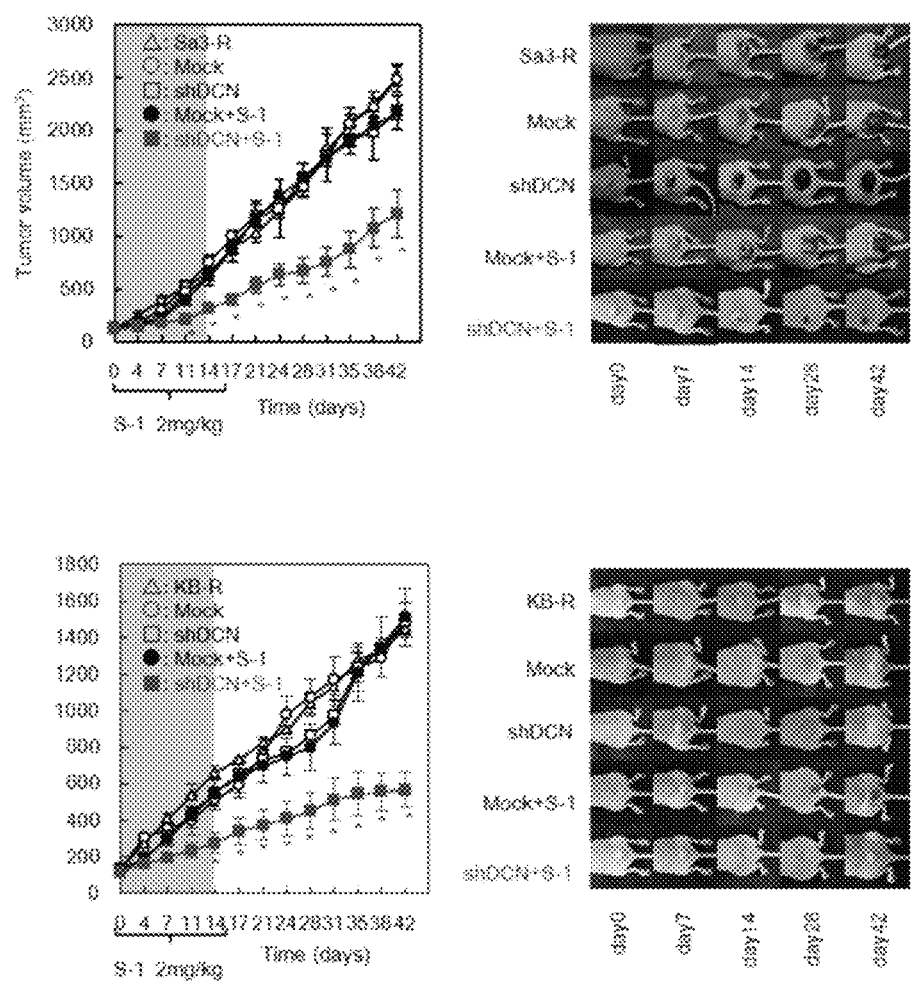
FIG. 6 shows the results of in vivo verification of the S-1 sensitivity of an shDCN cell line-derived tumor; the anticancer drug-resistant cell lines Sa-3R and KB-R that were highly expressing DCN, and Mock cell lines and shDCN cell lines thereof were each implanted into the back of nude mice to measure an oral administration effect of S-1; the two upper figures show the results for the Sa-3R line, and the two lower figures show the results for the KB-R line; in each of the cases using Sa-3R line and the KB-R line, a significant reduction in tumor volume was found in a group which was implanted with the shDCN cell line and orally administered with S-1 as compared to other groups.

FIG. 6 shows the results of the animal experiment. In an S-1 non-administered group, each of tumors derived from the Sa-3R line and the KB-R line, and the Mock cell line and shDCN cell line thereof showed similar tumor growth. Further, in the case of the oral administration of S-1, the tumor derived from the Mock cell line showed almost similar tumor growth to the tumor derived from each of the cell lines in the S-1 non-administered group because the Mock cell line had resistance to 5-FU. On the other hand, in the case of the oral administration of S-1, a significant decrease in tumor volume was found in the tumor derived from the shDCN cell line as compared to the above-mentioned four kinds of tumors.

FIG. 7 shows transitions in body weights of the mice subjected to the experiment. No significant change was found in the increase or decrease in body weight by the administration of S-1 and the suppressed expression of DCN.

The above-mentioned results revealed that the tumor derived from the shDCN cell line had increased sensitivity to S-1 in the in vivo experimental system. That is, it can be considered that the suppressed expression of DCN reduced the resistance of the tumors derived from the anticancer drug-resistant cell lines to S-1.

Immunohistological Feature of Tumor Derived from Cells with Suppressed Expression of DCN Pathological tissue sections of tumors derived from the cells with suppressed expression of DCN and control cells that were implanted into the nude mice were produced and subjected to immunohistochemical staining. In the immunohistological staining, a paraffin-embedded tissue fixed with formalin was cut into a slice having a thickness of 4 µm, subjected to deparaffinization treatment and dehydration treatment, then subjected to a reaction with 0.3% $H_2O_2$ for 30 minutes to remove an endogenous peroxidase, and further treated with 1.5% blocking serum (product of Santa Cruz Biotechnology, Inc.) to inhibit a reaction with a non-specific protein. After that, the resultant was subjected to a reaction with a PCNA polyclonal antibody (product of Santa Cruz Biotechnology, Inc.) diluted at a ratio of 1:50, an anti-AKT polyclonal antibody (product of Rockland Immunochemicals Inc.) diluted at a ratio of 1:500, and an anti-p-AKT (ser473) polyclonal antibody (product of Santa Cruz Biotechnology, Inc.) diluted at a ratio of 1:50 at 4° C. for 16 hours in a wet state. The resultant was washed three times with a phosphate buffer, subjected to a reaction with an EnVision reagent (product of Dako), and then subjected to color development with 3,3-diamonobenzidine tetrahydrochloride (product of Dako) to be detected. Finally, hematoxylin staining was performed for comparison. Further, apoptosis was studied with a TUNEL staining kit (product of Takara Bio Inc.).

An IHC score was used for the evaluation of staining property in the immunohistological staining. The IHC score is a total sum of numbers obtained by multiplying the percentage of positive cells in all cells in one field of view in observation with an objective lens having a magnification of 40 by the intensity of staining property. The intensity of staining property is evaluated, for example, on a three-point scale, i.e., "weak," "medium," and "strong," and the respective evaluations are assigned with integers of 1 to 3 to be converted to numerical values. This procedure is performed for 10 fields of view sampled at random, and an average value thereof is calculated as the IHC score. The IHC score is generally used in a method of determining staining degree at present as an excellent score showing a staining intensity and a staining range.

FIG. 8 shows the results of the TUNEL staining. There was a tendency that the ratio of apoptosis was high in tumor tissue sections of S-1 orally administered mice inoculated with the shDCN cell-derived tumor (shDCN·S-1(+)) as compared to tumor tissue sections of other control groups, i.e., S-1 non-administered mice inoculated with the shDCN cell-derived tumor (shDCN·S-1(−)) and S-1 administered mice and S-1 non-administered mice inoculated with the Mock cell line (Mock·S-1(+) and Mock·S-1(−), respectively).

Figure 9:
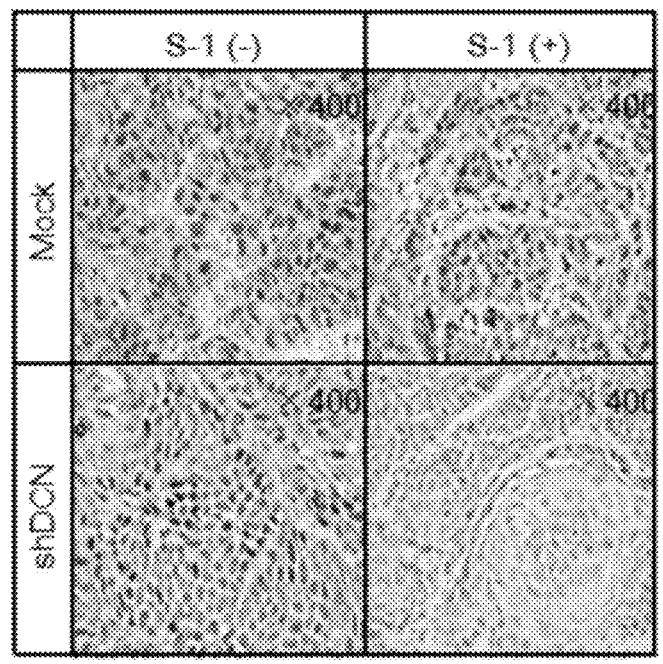
FIG. 9 shows the results of anti-proliferating cell nuclear antigen (hereinafter abbreviated as PCNA) immunohistological staining of tumor tissues implanted into the mice in the in vivo experiment in which the S-1 sensitivity of the shDCN cell line-derived tumor was verified; a clear decrease in cell growth was found in a group which was implanted with the shDCN cell line and orally administered with S-1 as compared to other groups.

FIG. 9 shows the results of the PCNA staining. There was a tendency that the ratio of cell growth was low in the shDCN·S-1(+) group as compared to the other control groups (shDCN·S-1(−), Mock·S-1(−), and Mock·S-1(+)).

Figure 10:
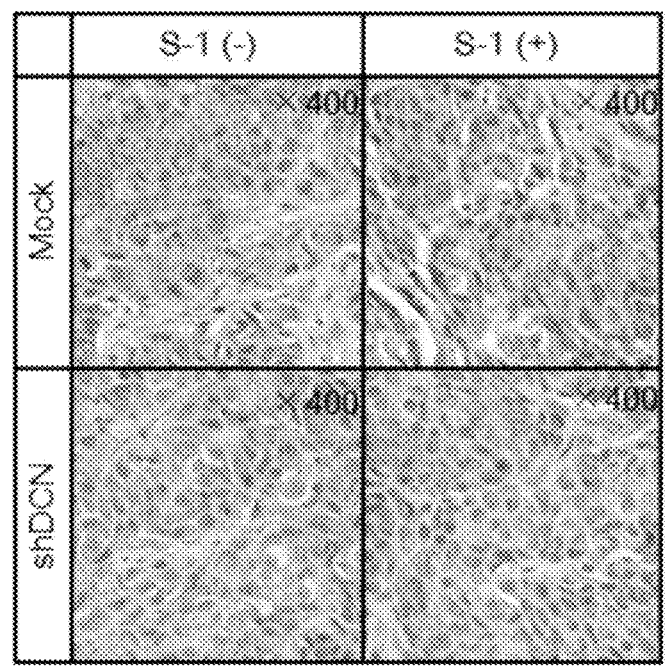
FIG. 10 shows the results of verification of the expression of AKT in the tumor tissue implanted into the mice by immunohistological staining in the in vivo experiment in which the S-1 sensitivity of the shDCN cell line-derived tumor was verified; there was no clear difference in the expression of AKT among all the groups.

FIG. 10 shows the results of the AKT staining. There was no difference in the expression of AKT between the S-1 administered and non-administered groups.

Figure 11:
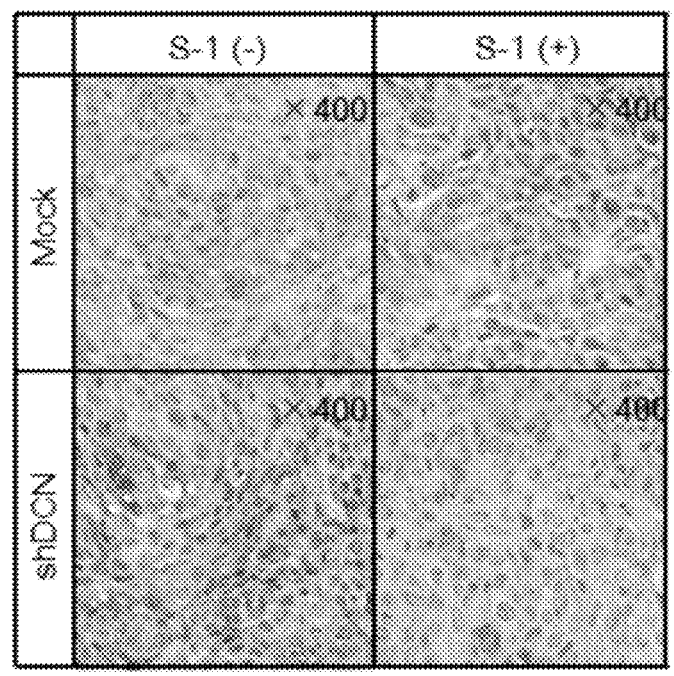
FIG. 11 shows the results of verification of the amounts of phosphorylated AKT (pAKT) in the tumor tissues implanted into the mice by immunohistological staining in the in vivo experiment in which the S-1 sensitivity of the shDCN cell line-derived tumor was verified; a decrease in the amount of phosphorylated AKT was found in a group which was implanted with the shDCN cell line and orally administered with S-1 as compared to other groups.

FIG. 11 shows the results of the p-AKT staining. There was a tendency that the amount of phosphorylated AKT decreased in the shDCN·S-1(+) group as compared to the other control groups (shDCN·S-1(−), Mock·S-1(−), and Mock·S-1(+)).

Figure 12:
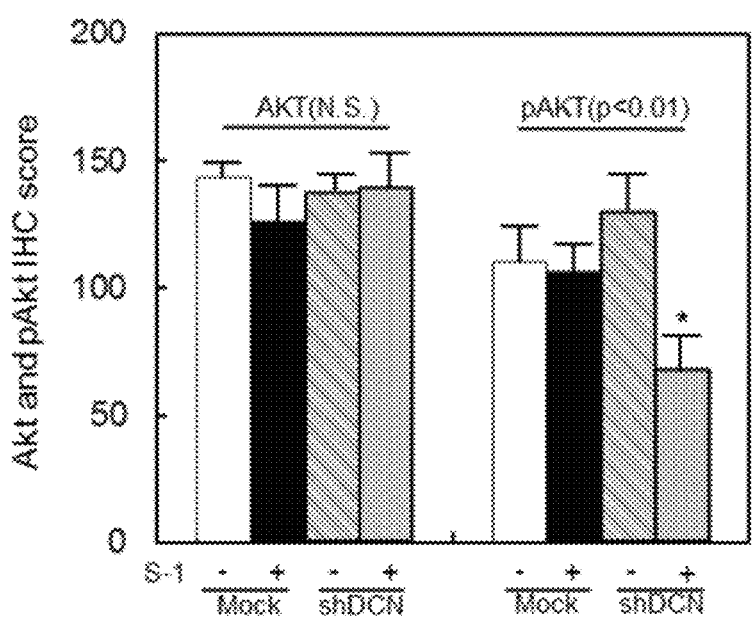
FIG. 12 shows the results of immunohistological staining (hereinafter sometimes abbreviated as IHC), which are presented by IHC scores analysed statistically, for detecting AKT and phosphorylated AKT (pAKT) in tissue sections of the tumor tissues implanted into mice in the in vivo experiment in which the S-1 sensitivity of the shDCN cell line-derived tumor was verified; no difference in the expression of AKT was found among the groups, while a significant decrease in the amount of pAKT was found in a group which was implanted with the shDCN cell line and orally administered with S-1 as compared to other groups.

FIG. 12 shows IHC scores of AKT and phosphorylated AKT. The IHC scores were calculated from FIG. 10 and FIG. 11. The IHC score of phosphorylated AKT significantly lowered in the shDCN·S-1(+) group.

The above-mentioned data suggested that the suppressed expression of DCN and the administration of S-1 resulted in the inhibition of AKT phosphorylation and the promotion of apoptosis.

Example 4

Relation Between Expression of DCN and Rate of Response to S-1 in Clinical Analyte A relation between the expression of DCN and the rate of response to S-1 in a clinical analyte was verified. In this example, a biological sample in any case was collected from a patient after informed consent had been performed to confirm the will of the patient.

The clinical analytes were tissue specimens collected by biopsy before carrying out chemotherapy. Tissue specimens from 16 head and neck cancer patients who received administration of S-1 after biopsy were used as the clinical analytes. The clinical analytes were 7 patients of a response group and 9 patients of a non-response group (SD/PD patient) to the administration of S-1. It should be noted that the patients sampled and investigated were patients having the same background. The response group means a patient with a complete response after the administration of S-1 as neoadjuvant chemotherapy (hereinafter referred to as CR patient). The non-response group means a patient with a stable disease in whom a certain effect was found but the effect was not sustained (hereinafter referred to as SD patient) and a patient with a progress disease (hereinafter referred to as PD patient) after the administration of S-1 as neoadjuvant chemotherapy.

First, in order to confirm the expression of DCN in vivo, the expression state of DCN was examined by immunohistological staining using a clinical analyte. The immunohistological staining was carried out by treating a section in accordance with a similar procedure to that of the method described in Example 3 using an anti-human DCN rabbit polyclonal antibody (product of Santa Cruz Biotechnology, Inc.) that is diluted at a ratio of 1:50. The expression of DCN was converted to a numerical value with the IHC score, and statistically analyzed by a Mann-Whitney's U test.

Figure 13:
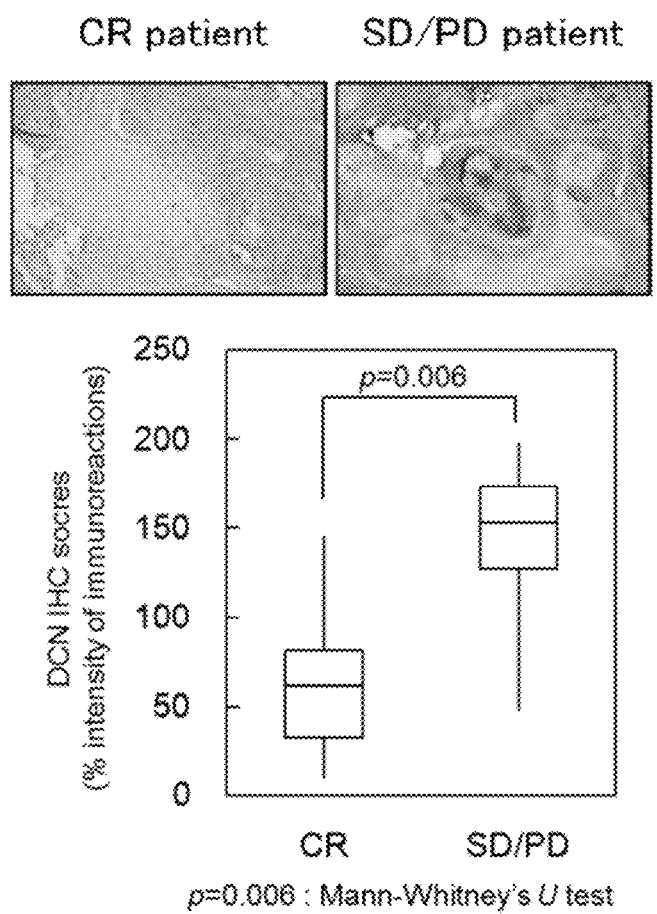
FIG. 13 shows the results of verification of the expression of DCN in biopsy samples before surgery from head and neck cancer patients by immunohistological staining, and distributions of IHC scores; by using tissue specimens from 16 patients who received administration of S-1 after biopsy, the expression of DCN was examined by immunohistological staining; the clinical analytes were 7 patients of a response group (CR group) and 9 patients of a non-response group (SD/PD group) to the administration of S-1; the upper figures show representative examples of the immunohistological staining of the CR group and the SD/PD group, respectively; the lower figure shows distributions of DCN IHC scores (% intensity of immunoreactions) of the respective groups; the expression of DCN was found to be significantly enhanced in the SD/PD group as compared to the CR group, suggesting that the expression level of DCN was correlated with a response rate to the administration of S-1.

FIG. 13 shows representative examples of the results of immunohistological staining of DCN in the clinical analytes from the 16 patients, and distributions of IHC scores of the CR patients and the SD/PD patients. The expression of DCN was weak in the CR patient who showed a response to the administration of S-1. On the other hand, the enhanced expression of DCN was found in the SD/PD patients where the effect of S-1 was insufficient. Further, the IHC score of DCN in the SD/PD patients was significantly high as compared to the IHC score in the CR patients (P=0.006).

The above-mentioned results revealed that there was a correlation between the expression of DCN in a biopsy sample from a cancer patient and the rate of response to the administration of S-1.

Next, in order to determine an objective evaluation scale for the rate of response to the administration of S-1, cutoff values were calculated from the results of the IHC scores for the CR patients and the SD/PD patients. Various techniques for calculating the cutoff values are known. Of those, a technique using a receiver operating characteristic curve (ROC curve) was used in this study. The ROC curve is utilized as a technique for investigating the usefulness of a diagnosis inspection, and is a curve obtained by plotting a sensitivity at each threshold on the axis of ordinate and plotting a false positive fraction (FPF: 1-specificity) on the axis of abscissa when the threshold is changed. In the ROC curve, an inspection having no diagnosis ability gives a straight line on a diagonal line. As the diagnosis ability improves more, the diagonal line turns into a curve convex toward the upper left direction, and an inspection having a diagnosis ability of 100% gives a curve passing through the left side and the upper side.

Figure 14:
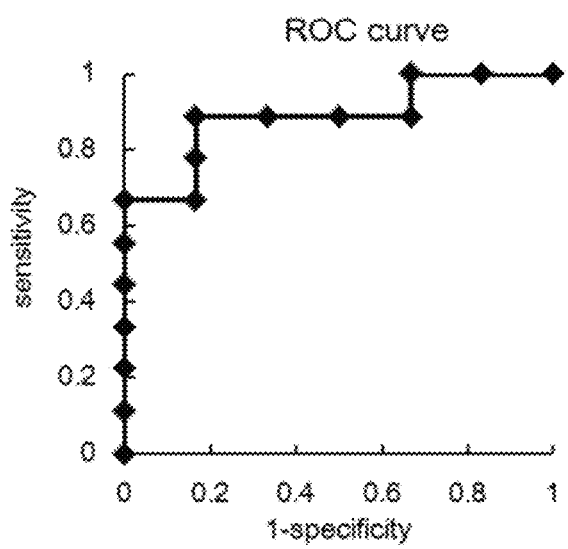
FIG. 14 shows the results of cutoff values for the DCN IHC scores found in the biopsy samples determined by an ROC curve in the CR group and SD/PD group of the head and neck cancer patients who received administration of S-1 after biopsy.

FIG. 14 shows an ROC curve determined from the IHC scores of the clinical analytes from the CR patient group and the SD/PD patient group. A relation between the IHC score and the rate of response to the administration of S-1 is evaluated by the area under the curve (abbreviated as AUC) in the ROC curve, and its value is generally 0.5 to 1.0. The result of the AUC was 0.889 in this study. In general, the AUC is used as an indicator for assessing a prediction ability and diagnosis ability, and is evaluated on a three-point scale. That is, the prediction ability or the diagnosis ability is evaluated to be low when the AUC is 0.5 to 0.7, to be moderate when the AUC is 0.7 to 0.9, and to be high when the AUC is 0.9 to 1.0. Thus, the prediction and diagnosis abilities based on the IHC score between the two groups in the results of this study were found to be relatively high.

In order to calculate a cutoff value based on the ROC curve used in this study, two kinds of techniques were used for determining a cutoff value for convenience in view of a balance between sensitivity and specificity.

The first method is a method comprising setting a point at which a distance from the upper left corner becomes minimum as a cutoff value based on the fact that an ROC curve of an inspection which is excellent in sensitivity and specificity and has a high diagnosis ability moves closer to the upper left corner. When a point at which a distance from the point at the upper left corner of the graph of the ROC curve shown in FIG. 14 to the curve becomes smallest is determined from the curve, a cutoff value for the IHC score is 119, and the sensitivity and specificity at this time were 0.889 and 0.833 (false positive fraction: 0.167), respectively.

Figure 15:
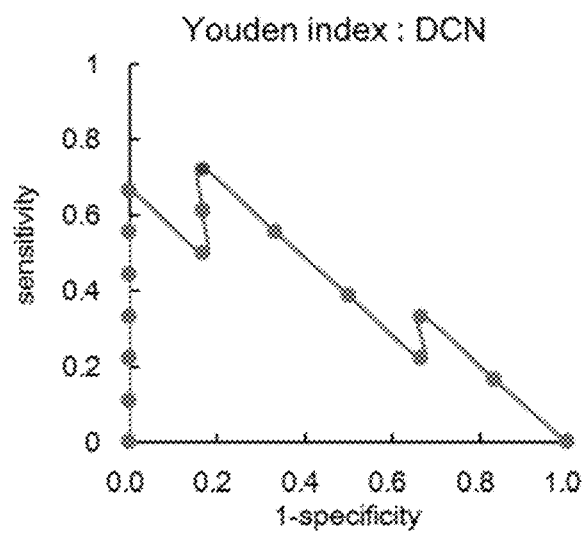
FIG. 15 shows the results of cutoff values for the DCN IHC scores found in the biopsy samples determined with a Youden index in the CR group and SD/PD group of the head and neck cancer patients who received administration of S-1 after biopsy.

The second method is a technique based on the idea opposite to the foregoing, and is a method involving setting, as a cutoff value, a point most distant from an ROC curve of an inspection estimated to have lowest prediction and diagnosis abilities, i.e., a diagonal dotted line corresponding to AUC=0.500. That is, the method is a method involving calculating a value of (sensitivity+specificity−1) and setting a point at which the value becomes maximum as a cutoff value, and this point is called a Youden index. A cutoff value for the IHC score determined with the Youden index shown in FIG. 15 by the second technique was 119, and the sensitivity and specificity at this time were 0.889 and 0.833 (false positive fraction: 0.167), respectively, which were similar results to those in the first technique.

The above-mentioned results suggested that the sensitivity to the administration of S-1 was able to be foreseen from the expression state of DCN in the biopsy sample at a high probability by using the cutoff value for the IHC score determined from the expression of DCN, specifically, the cutoff value of 119.

As shown in Examples 1 to 3, the verification using experimental systems using the anticancer drug-resistant cell lines and cancer-bearing mice revealed that the expression of DCN was deeply involved in anticancer drug resistance. In addition, the verification showed that the sensitivity to S-1 was able to be assessed before the administration of S-1 by analyzing the expression state of DCN using the biopsy sample.

The present invention includes determining, before carrying out chemotherapy with S-1 in a cancer patient, whether cancer cells of the cancer patient are resistant or sensitive to the chemotherapy, and can be utilized in a clinical diagnostic industry, a reagent industry, and a medical device industry.

SEQ ID NO: 1 human decorin gene

What is claimed is:

1. A method of administering chemotherapy with S-1 for a subject in need of chemotherapy, the method comprising:
    a step (a) of collecting a biological sample from a subject before carrying out chemotherapy with S-1, wherein S-1 is obtained by blending tegafur, gimeracil, and oteracil potassium as active ingredients, the biological sample comprises a cancer tissue, and the biological sample is from a head and neck squamous cell carcinoma patient or an oral squamous cell carcinoma patient;
    a step (b) of measuring expression level of a decorin gene in the biological sample collected from the subject before carrying out the chemotherapy with S-1;
    a step (c) of predicting an administration effect of S-1 using a predetermined reference value wherein the subject is assessed to have resistance to S-1 when the expression level of the decorin gene in the biological sample is high as compared to the predetermined reference value, while the subject is assessed to have sensitivity to S-1 when the expression level of the decorin gene is low as compared to the predetermined reference value;
    a step (d) of identifying the subject as having the sensitivity to S-1; and
    a step (e) administering said chemotherapy with S-1 to the subject assessed to have the sensitivity to S-1.

2. A method of administering chemotherapy with S-1 according to claim 1, wherein the step (b) comprises measuring a protein as a product of the gene.

3. A method of administering chemotherapy with S-1 according to claim 1, wherein the step (b) comprises measuring an amount of mRNA of the gene.

4. A method of administering chemotherapy with S-1 for a subject in need of chemotherapy, the method comprising:
- a step (a) of collecting a biological sample from a head and neck cancer patient before carrying out chemotherapy with S-1, wherein S-1 is obtained by blending tegafur, gimeracil, and oteracil potassium as active ingredients, the biological sample comprises a cancer tissue, and the biological sample is from a head and neck squamous cell carcinoma patient or an oral squamous cell carcinoma patient;
- a step (b) of measuring an expression amount of a decorin protein in the biological sample collected from the head and neck cancer patient before carrying out chemotherapy with S-1;
- a step (c) of predicting an administration effect of S-1 using a predetermined reference value wherein the subject is assessed to have resistance to S-1 when the expression level of a decorin gene in the biological sample is high as compared to the predetermined reference value, while the subject is assessed to have sensitivity to S-1 when the expression level of the decorin gene is low as compared to the predetermined reference value;
- a step (d) of identifying the subject as having the sensitivity to S-1; and
- a step (e) administering said chemotherapy with S-1 to the subject assessed to have the sensitivity to S-1.

5. A method of administering chemotherapy with S-1 for a subject in need of chemotherapy, the method comprising:
- a step (a) of collecting a biological sample from a head and neck cancer patient before carrying out chemotherapy with S-1, wherein S-1 is obtained by blending tegafur, gimeracil, and oteracil potassium as active ingredients, the biological sample comprises a cancer tissue, and the biological sample is from a head and neck squamous cell carcinoma patient or an oral squamous cell carcinoma patient;
- a step (b) of measuring an expression amount of a decorin protein in the biological sample collected from the head and neck cancer patient before carrying out chemotherapy with S-1 by immunohistological staining using an anti-decorin protein antibody;
- a step (c) of predicting an administration effect of S-1 using a cutoff value for an immunohistochemical staining (IHC) score obtained from the measurement, wherein the cutoff value is 119, the subject having a sensitivity to S-1 when the expression amount is equal to or less than the cutoff value;
- a step (d) of identifying the subject as having a sensitivity to S-1; and
- a step (e) administering said chemotherapy with S-1 to the subject assessed to have sensitivity to S-1.

6. A method of administering chemotherapy with an anticancer drug for a subject in need of chemotherapy, the method comprising:
- collecting a biological sample from a subject before carrying out chemotherapy with 5-fluorouracil, the biological sample comprises a cancer tissue, and the biological sample is from a head and neck squamous cell carcinoma patient or an oral squamous cell carcinoma patient;
- measuring expression level of a decorin gene in the biological sample collected from the subject before carrying out chemotherapy with 5-fluorouracil;
- predicting an administration effect of 5-fluorouracil using a predetermined reference value wherein the subject is assessed to have resistance to 5-fluorouracil when the expression level of the decorin gene in the biological sample is high as compared to the predetermined reference value, while the subject is assessed to have sensitivity to 5-fluorouracil when the expression level of the decorin gene is low as compared to the predetermined reference value;
- identifying the subject as having the sensitivity to 5-fluorouracil; and
- administering said chemotherapy with 5-fluorouracil to the subject assessed to have the sensitivity to 5-fluorouracil.

7. A method of administering chemotherapy with S-1 for a subject in need of chemotherapy, the method comprising:
- a step (a) of selecting a cutoff value for decorin gene expression above which S-1 is resisted as a chemotherapy, S-1 being a chemotherapeutic composition comprising tegafur, gimeracil, and oteracil potassium as active ingredients;
- a step (b) of measuring an expression level of the decorin gene in a biological sample collected from a subject, the biological sample comprising a cancer tissue, wherein the biological sample is from a head and neck squamous cell carcinoma patient or an oral squamous cell carcinoma patient;
- a step (c) of determining the presence or absence of S-1 resistance of the subject based on the measurement;
- a step (d) of identifying the subject as having the absence of S-1 resistance; and
- a step (e) administering said chemotherapy with S-1 to the subject assessed to have the absence of S-1 resistance.

* * * * *